(12) United States Patent
Tüzüner et al.

(10) Patent No.: US 11,432,854 B2
(45) Date of Patent: Sep. 6, 2022

(54) EXTENSION DRIVE MECHANISM FOR INTRAMEDULLARY EXTENSION NAILS

(71) Applicants: Desird Tasarim Arge Uygulama Elektronik Destek Ithalat Ihracat Sanayi Ve Ticaret Limited Sirketi, Antalya (TR); Serdar Tüzüner, Antalya (TR)

(72) Inventors: Serdar Tüzüner, Antalya (TR); Emre Çiftçi, Antalya (TR)

(*) Notice: Subject to any disclaimer, the term of this patent is extended or adjusted under 35 U.S.C. 154(b) by 0 days.

(21) Appl. No.: 17/294,551

(22) PCT Filed: Mar. 13, 2020

(86) PCT No.: PCT/TR2020/050201
§ 371 (c)(1),
(2) Date: May 17, 2021

(87) PCT Pub. No.: WO2020/190239
PCT Pub. Date: Sep. 24, 2020

(65) Prior Publication Data
US 2022/0015809 A1 Jan. 20, 2022

(30) Foreign Application Priority Data

Mar. 15, 2019 (TR) .................................. 2019/03928
Mar. 2, 2020 (TR) .................................. 2020/03213

(51) Int. Cl.
A61B 17/72 (2006.01)
A61B 17/88 (2006.01)

(52) U.S. Cl.
CPC ...... A61B 17/7216 (2013.01); A61B 17/8875 (2013.01)

(58) Field of Classification Search
CPC . A61B 17/72; A61B 17/7216; A61B 17/7225; A61B 2017/681
USPC .............................................. 606/62, 63, 105
See application file for complete search history.

(56) References Cited

U.S. PATENT DOCUMENTS

| | | | |
|---|---|---|---|
| 4,926,708 A | 5/1990 | Dietrich et al. | |
| 6,245,075 B1 | 6/2001 | Betz et al. | |
| 2012/0130428 A1* | 5/2012 | Hunziker | ........... A61B 17/7016 606/258 |

FOREIGN PATENT DOCUMENTS

| | | |
|---|---|---|
| EP | 0432253 B1 | 10/1996 |
| TR | 201309996 U | 2/2014 |
| WO | 2018125980 A1 | 7/2018 |

OTHER PUBLICATIONS

International Search Report and Written Opinion of the International Searching Authorityfor corresponding PCT/TR2020/050201, dated Jul. 20, 2020.

* cited by examiner

Primary Examiner — Eduardo C Robert
Assistant Examiner — Christina Negrellirodriguez
(74) Attorney, Agent, or Firm — Egbert, McDaniel & Swartz, PLLC

(57) ABSTRACT

An extension drive mechanism which enables the intramedullary nails used in the orthopedic surgery in the bone extension nail systems to extend and shorten in the application area and enables the bone to extend or shorten in a controlled manner.

5 Claims, 2 Drawing Sheets

EXTENSION DRIVE MECHANISM FOR INTRAMEDULLARY EXTENSION NAILS

TECHNICAL FIELD

Figure 1:
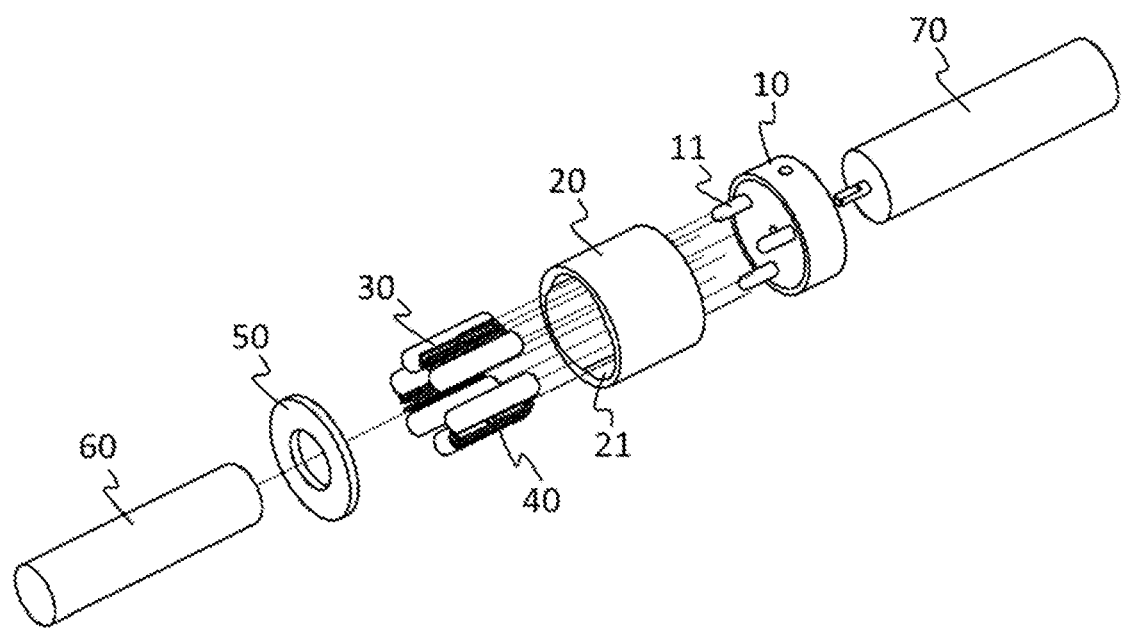

The invention is related to the extension drive mechanism used in the bone extension nail systems in the orthopedic surgery.

The invention is particularly related to extension drive mechanism which enables the intramedullary nails to extend and shorten in the application area and enables the bone to extend or shorten in a controlled manner.

STATE OF THE ART

In the orthopedic surgery in the treatment of lower extremity shortness, bone extension methods with different techniques are applied in vivo and in vitro. There are many different advantages and disadvantages of these extension techniques. The biggest problem of the in vitro methods is that the patients are open to infection. The intramedullary nails which are located inside the body lead to many different problems in the control and application regions.

In the present state of the art, the extensible nail system are generally divided into two namely the mechanically controlled systems and motor controlled systems.

The mechanically controlled systems are generally the systems that have mechanical structure and can be extended by the movement of the legs of the patient. In said systems, the length of the nail can be extended in an uncontrolled manner even by the uncontrolled leg motions of the patient during walking and sleeping or after a very difficult stretching during a painful period. In addition, the extension amount is not known exactly, also based on the system structure, since it covers a long area in the leg, it leads to less extension in the length of the nails.

Motor controlled nail systems are the state of the art technology and the most effective bone extension systems. With the motor controlled nail systems, the required extension amount of the intramedullary nail placed in the bone can be adjusted by the motor control. In said systems, a motor is placed in the nail and the motor is moved by means of feeding thereof by an exterior energy source or movement is provided by only locating the rotor section inside the nail and by creating a magnetic field in the form of a module outside the body with the stator part.

Mechanically controlled systems are not appropriate for thin bones due to their high cost and their occupying a lot of space with their motor and rotor systems. After the intramedullary nail system is placed inside the body, after the bone osteotomy process, since the opening between two bones cannot be eliminated or reduced, approximately two to four-week waiting period is required.

Document No EP0432253B1 can be shown as an example to the state of the art in the research made in the literature. Said document is related to an intramedullary nail which is extended in a progressive manner. Said intramedullary nail generally comprises a pipe, cylindrical rods which move by sliding on each other by means of a threaded sleeve within the pipe, a tube which is connected to the threaded sleeve within the pipe by means of a screw. The extension of the tube is provided with its forward movement depending on its connection with the threaded sleeve and screw within the pipe. However, since said assembly is large based on its structure, it causes more medullar channel carving in the region where it is applied and even it is not possible to apply in the narrow bone structures. It is required that the rotation motion is quite long and difficult due to the mechanism structure provided with the threaded sleeve and threaded thread. It can be possible in elder or overweight patients that the desired efficiency cannot be achieved.

As a result, in order to solve the abovementioned problems and the insufficiency of the current solutions makes it necessary to make a development in the relevant technical field.

AIM OF THE INVENTION

The present invention is related to an extension drive mechanism for the intramedullary extension nails which eliminates the abovementioned disadvantages and brings new advantages to the relevant technical field.

The main aim of the invention is to enable the bone to extend or shorten in a controlled manner by providing the intramedullary nails to extend and shorten in the application area.

The aim of the invention is to obtain an extension drive mechanism which allows the bone extension amount only when required until it reaches the desired length based on the movements of the patient and stops the extension of the nail even if the patient moves by fixing thereof when the required size is obtained.

Another aim of the invention is to enable the required compression in the early stages of recovery.

Another aim of the invention is to provide ease of application for thin bones due to its small external diameter.

Another aim of the invention is to provide the bone extension amount reaching up to 100 mm.

Another aim of the invention is to provide the bone lengthening process is accelerated, stopped or shortened by the desired amount if necessary, after the extension operation begins if the nail is less or more than the planned extension speed in radiological evaluations made during clinical controls.

In order to fulfill all aims that may arise from the abovementioned and detailed description, the invention is related to an extension drive mechanism which enables the intramedullary nails used in the orthopedic surgery in the bone extension nail systems to extend and shorten in the application area and enables the bone to extend or shorten in a controlled manner. The invention is characterized in that, it comprises the following;

- a direction control part which has direction control pins on its bottom surface, has rotational movement,
- a bearing housing which is located on the bottom surface of the direction control part and has internal movement surfaces on its internal surface,
- needle bearings which are located within each of the internal movement surfaces in the bearing housing in the form of at least pairs and whose axes are changed by moving by means of the direction control pins,
- bearing springs which are located between the needle bearings and enable the needle bearings to remain separate by pushing each other from the side surface,
- a drive shaft which is located between the needle bearings from the lower end of the bearing housing and rotates clockwise or counterclockwise by the needle bearings,
- gear motor which is engaged with the upper end of the direction control part and enables the direction control part to be driven in the selected rotational direction for rotating the drive shaft.

The structural and characteristic features of the present invention will be understood clearly by the following drawings and the detailed description made with reference to

FIGURES CLARIFYING THE INVENTION

FIG. 1: is the exploded perspective view of the inventive extension drive mechanism.

Figure 2:
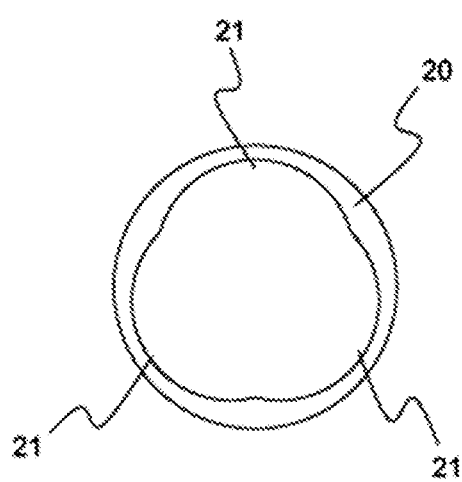

FIG. 2: is the front view of the bearing housing of the inventive extension drive mechanism.

Figure 3:
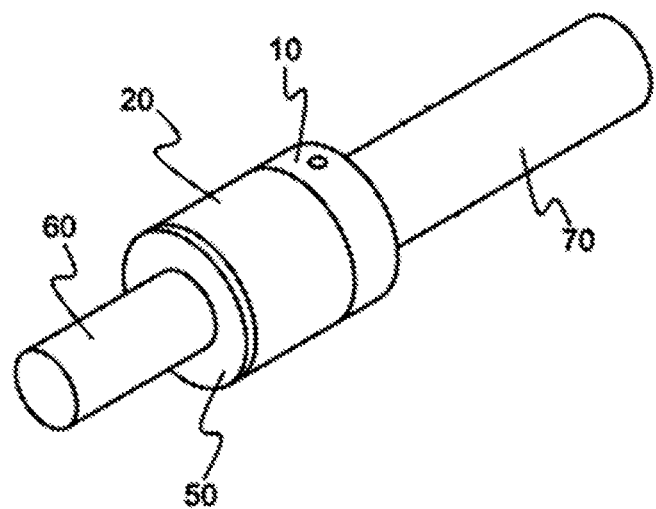

FIG. 3: is the perspective view of the inventive extension drive mechanism.

Figure 4:
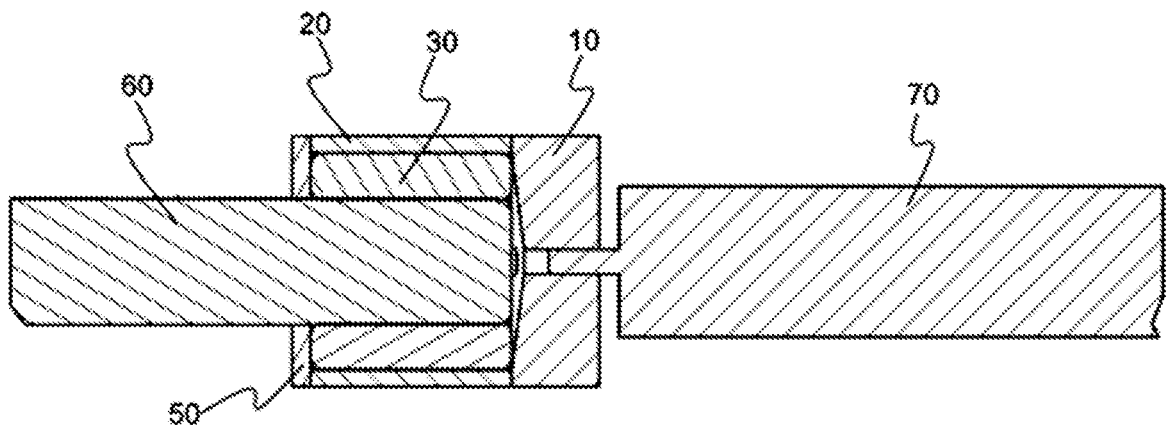

FIG. 4: is the sectional view of the inventive extension drive mechanism.

DESCRIPTION OF THE PART REFERENCES

10. Direction control part
11. Direction control pin
20. Bearing housing
21. Internal movement surface
30. Needle bearing
40. Bearing spring
50. Bearing protection cover
60. Drive shaft
70. Gear motor

DETAILED DESCRIPTION OF THE INVENTION

In this detailed description, the preferred alternatives of the inventive extension drive mechanism is described only for clarifying the subject manner such that no limiting effect is created.

In FIG. 1, the exploded perspective view of the inventive extension drive mechanism is given. Accordingly, the extension drive mechanism mainly comprises the following; a direction control part (10) which has direction control pins (11) on its bottom surface located at 120° angles to each other, has rotational movement, a bearing housing (20) which is located on the bottom surface of the direction control part (10) and has an internal movement surface (21) whose internal surface is located with 120° angle and is formed from three circles with different centers, needle bearings (30) which are located within each of the internal movement surfaces (21) in the bearing housing (20) in the form of at least pairs and whose axes are changed by moving by means of the direction control pins (11), bearing springs (40) which are located between the needle bearings (30), a bearing protection cover (50) which is engaged to the bottom surface of said bearing housing (20), a drive shaft (60) which is located between the needle bearings (30) from the lower end of the bearing housing (20) and rotates clockwise or counterclockwise, a gear motor (70) which is engaged with the upper end of the direction control part (10) and enables the direction control part (10) to be driven in the selected rotational direction for rotating the drive shaft (60).

The direction control part (10) on its lower surface has direction control pins (11) which are located at 120° angles to each other. The bearing housing (20) is connected to the bottom surface of the direction control part (10). As can be seen in FIG. 2, the internal surface of the bearing housing (20) has an internal movement surface (21) which is the combination of three different circles with different centers placed at an angle of 120° to each other.

There are needle bearings (30) within each of the internal movement surfaces (21) in the bearing housing (20), in the form of pairs and 6 in total. Said needle bearings (30) remain parallel to each other in the bearing housing (20) in the axes of their own internal movement surfaces (21). Bearing springs (40) are located between the needle bearings (30) and the needle bearings (30) which are in the form of pairs within the internal movement surfaces (21) are provided to remain separate by pushing each other from the side surface.

In order to change the operational axes of the needle bearings (30), direction control pins (11) in the direction control part (10) located on the upper surface of the bearing housing (20) is located between the needle bearings (30) which are available in the form of pairs in the internal movement surfaces (21) in the bearing housing (20).

The needle bearings (30) move in the internal movement surfaces (21) by means of the direction control pins (11) which are located on the bottom surface of the direction control part (10) and can move clockwise or counterclockwise on the central axis. Said direction control part (10) can be able to move with an angle of ±5° to ±10° clockwise or counterclockwise on the centra I axis. The direction control part (10) which is engaged with the bearing housing (20) at its bottom end receives its rotational motion from the gear motor (70) which is engaged to its upper end.

The bottom surface of the bearing housing (20) is closed with the bearing protection cover (50) which prevents the bearing springs (40) to come out of the bearing housing (20) by means of the needle bearings (30).

A drive shaft (60) is located on the center of the bearing housing (20) such that it is located in the lower end of the bearing housing (20). Said drive shaft (60) can rotate clockwise or counterclockwise depending on the movement of the needle bearings (30) within the bearing housing (20).

The operation principle of the extension drive mechanism subject to the invention seen in FIG. 3 is as follows;

Said direction control part (10) is moved with an angle of ±5° to ±10° clockwise or counterclockwise by means of the gear motor (70). Depending on the rotational movement of the direction control part (10), also the directions control pins (11) which are located between the needle bearings (30) available in the form of pairs within the internal movement surfaces (21) in the bearing housing (20) move in the same manner.

The axes of the needle bearings (30) change with their movement in the internal movement surfaces (21) depending on the rotational movement of the direction control pins (11). The needle bearings (30) whose axes change in the internal movement surfaces (21) rotate the drive shaft (60) in the rotational direction.

As can be seen in FIG. 4, in case the direction control pins (11) are in the middle point of each needle bearing (30) pair namely at 0°, the drive shaft (60) cannot move in both directions.

The invention claimed is:

1. An extension drive mechanism for causing an intramedullary nail to extend or to retract in an application area so as to enable a bone to extend or to retract in a controlled manner, the extension drive mechanism comprising:
    a direction control part having direction control pins on a bottom surface thereof, said direction control part being rotatable;
    a bearing housing positioned on the bottom surface of said direction control part, said bearing housing having movement surfaces on an interior thereof;
    a plurality of needle bearings positioned within each of the movement surfaces in said bearing housing, said plurality of needle bearings being arranged in at least pairs and having respective axes that are changeable by the direction control pins;

a plurality of bearing springs positioned respectively between said plurality of needle bearings, said plurality of bearing springs separating respectively said plurality of needle bearings by urging against a side surface of the needle bearing;

a drive shaft positioned between said plurality of needle bearings from a lower end of said bearing housing, said plurality of needle bearings causing said drive shaft to rotate either clockwise or counterclockwise by said plurality of needle bearings; and a gear motor engaged with an upper end of said direction control part, said gear motor cooperative with said direction control part so as to cause said direction control part to be driven in said desired rotational direction for rotating said drive shaft.

2. The extension drive mechanism of claim 1, wherein the movement surfaces are in a form of three different circles having respective different centers positioned at an angle of 120° with respect to each other.

3. The extension drive mechanism of claim 1, wherein the direction control pins of said direction control part are arranged at a 120° angle with respect to each other, the direction control pins positioned respectively between said plurality of needle bearings in the movement surfaces so as to move said plurality of needle bearings.

4. The extension drive mechanism of claim 1, wherein said drive shaft is rotatable when the direction control pins of said direction control part are driven by said gear motor.

5. The extension drive mechanism of claim 1, further comprising:

a bearing protection cover engaged with a bottom surface of said bearing housing, said bearing protection cover adapted to prevent said plurality of bearing springs from coming out of said bearing housing.

\* \* \* \* \*